(12) United States Patent
Veeraraghavan et al.

(10) Patent No.: US 10,753,869 B2
(45) Date of Patent: Aug. 25, 2020

(54) LENSLESS IMAGING DEVICE FOR MICROSCOPY AND FINGERPRINT BIOMETRIC

(71) Applicant: William Marsh Rice University, Houston, TX (US)

(72) Inventors: Ashok Veeraraghavan, Houston, TX (US); Richard Baraniuk, Houston, TX (US); Jacob Robinson, Houston, TX (US); Vivek Boominathan, Houston, TX (US); Jesse Adams, Houston, TX (US); Benjamin Avants, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 16/321,309

(22) PCT Filed: Jul. 28, 2017

(86) PCT No.: PCT/US2017/044448
§ 371 (c)(1),
(2) Date: Jan. 28, 2019

(87) PCT Pub. No.: WO2018/023039
PCT Pub. Date: Feb. 1, 2018

(65) Prior Publication Data
US 2019/0178796 A1    Jun. 13, 2019

Related U.S. Application Data

(60) Provisional application No. 62/368,618, filed on Jul. 29, 2016.

(51) Int. Cl.
*G01N 21/47* (2006.01)
*A61B 5/00* (2006.01)
*G06K 9/00* (2006.01)
*G02B 21/36* (2006.01)
(Continued)

(52) U.S. Cl.
CPC ....... *G01N 21/4795* (2013.01); *A61B 5/0059* (2013.01); *G01N 21/6458* (2013.01);
(Continued)

(58) Field of Classification Search
None
See application file for complete search history.

(56) References Cited

U.S. PATENT DOCUMENTS

2003/0091147 A1* 5/2003 Takata ............... G01N 23/2076
378/71
2008/0095298 A1* 4/2008 Shefsky .................. G01T 1/295
378/2

(Continued)

FOREIGN PATENT DOCUMENTS

EP        1883839 A1    2/2008

OTHER PUBLICATIONS

M. Salman Asif et al: "Flatcam: Thin, Bare-Sensor Cameras using Coded Aperture and Computation" Aug. 31, 2015 (12 pages).
(Continued)

*Primary Examiner* — Talha M Nawaz
(74) *Attorney, Agent, or Firm* — Osha Liang LLP (57) ABSTRACT

In one aspect, embodiments disclosed herein relate to a lens-free imaging system. The lens-free imaging system includes: an image sampler, a radiation source, a mask disposed between the image sampler and a scene, and an image sampler processor. The image sampler processor obtains signals from the image sampler that is exposed, through the mask, to radiation scattered by the scene which is illuminated by the radiation source. The image sampler processor then estimates an image of the scene based on the signals from the image sampler, processed using a transfer function that relates the signals and the scene.

17 Claims, 9 Drawing Sheets

(51) Int. Cl.
| | |
|---|---|
| *G01N 21/64* | (2006.01) |
| *G01N 21/76* | (2006.01) |
| *G06T 7/55* | (2017.01) |
| *G02B 21/16* | (2006.01) |
| *A61B 5/1172* | (2016.01) |
| *G02B 21/00* | (2006.01) |
| *A61B 90/20* | (2016.01) |

(52) U.S. Cl.
CPC ............ *G01N 21/763* (2013.01); *G02B 21/16* (2013.01); *G02B 21/361* (2013.01); *G02B 21/367* (2013.01); *G06K 9/00013* (2013.01); *G06T 7/55* (2017.01); *A61B 5/0071* (2013.01); *A61B 5/0077* (2013.01); *A61B 5/1172* (2013.01); *A61B 90/20* (2016.02); *G02B 21/0008* (2013.01); *G06T 2207/10048* (2013.01); *G06T 2207/10056* (2013.01); *G06T 2207/30024* (2013.01)

(56) References Cited

U.S. PATENT DOCUMENTS

2009/0095912 A1* 4/2009 Slinger .................. G02B 27/00
250/363.06
2012/0086794 A1 4/2012 Burcham et al.

OTHER PUBLICATIONS

Khademhosseinieh Bahar et al: "Lensfree on-chip imaging using nanostructured surfaces", Applied Physics Letters, A I P Publishing LLC, US, vol. 96, No. 17, Apr. 30, 2010 (3 pages).
International Search Report issued in International Application No. PCT/US2017/044448 dated Oct. 10, 2017 (4 pages).
Written Opinion issued in International Application No. PCT/US2017/044448 dated Oct. 10, 2017 (9 pages).

* cited by examiner

LENSLESS IMAGING DEVICE FOR MICROSCOPY AND FINGERPRINT BIOMETRIC

CROSS-REFERENCE TO RELATED APPLICATIONS

This application claims priority to U.S. Provisional Patent Application No. 62/368,618 filed Jul. 29, 2017, the entire disclosure of which is hereby expressly incorporated by reference herein.

STATEMENT REGARDING FEDERALLY SPONSORED RESEARCH OR DEVELOPMENT

The invention was made with government support under Grant Number CCF-1527501 awarded by the National Science Foundation, N00014-15-1-2878 awarded by the Department of Defense, and EAGER awarded by the National Science Foundation. The government has certain rights in the invention.

BACKGROUND

Imaging devices such as microscopes are used in various disciplines, such as biology. However, traditional microscopes suffer from a fundamental tradeoff between size and performance. More specifically, down-sizing conventional microscopes typically results in the collection of less light and/or the imaging of a smaller field of view. Overcoming this tradeoff would be desirable and would make microscopy suitable for novel applications.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a lens-free imaging system. The lens-free imaging system includes an image sampler; a radiation source; a mask disposed between the image sampler and a scene; and an image sampler processor that: obtains signals from the image sampler that is exposed, through the mask, to radiation scattered by the scene, wherein the scene is illuminated by the radiation source; and estimates an image of the scene based on the signals from the image sampler, processed using a transfer function that relates the signals and the scene.

In another aspect, embodiments of the present disclosure relate to methods for generating an image of a scene using a lens-free imaging system. The method includes: obtaining signals from an image sampler that is exposed, through a mask, to radiation scattered by the scene; and estimating the image of the scene, based on the signals from the image sampler, processed using a transfer function that relates the signals and the scene.

BRIEF DESCRIPTION OF DRAWINGS

Certain embodiments of the invention will be described with reference to the accompanying drawings. However, the accompanying drawings illustrate only certain aspects or implementations of the invention by way of example and are not meant to limit the scope of the claims.

DETAILED DESCRIPTION

Specific embodiments of the invention will now be described in detail with reference to the accompanying figures. Like elements in the various figures are denoted by like reference numerals for consistency. Like elements may not be labeled in all figures for the sake of simplicity.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-9, any component described with regard to a figure, in various embodiments of the technology, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments of the technology, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that, one or more of the steps shown in the flowcharts may be omitted, repeated, and/or performed in a different order than the order shown. Accordingly, the scope of the invention should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

Embodiments of the invention relate to lens-less imaging systems, lens-less imaging sensors, and methods of operating lens-less imaging systems. A lens-less imaging system may generate electrical signals in response to receiving electromagnetic (EM) radiation. The electrical signals generated by the lens-less imaging system may be processed to generate an image of a scene from which the electromagnetic energy was scattered.

In one or more embodiments of the invention, a lens-less imaging system may include an image sampler, one or more masks, a radiation source, and an image sampler processor. Each of the aforementioned components may be used to generate an image of a scene. The image sampler may generate electronic signals in response to receiving EM radiation. The image sampler may be, for example, a charge capture device (CCD) that responds to EM radiation. In one or more embodiments of the invention, the image sampler may be a sensor. In one or more embodiments of the invention, the sensor may be a sensor array. Other devices may be used as the image sampler without departing from the invention.

In one or more embodiments of the invention, the EM radiation may be visible light, short-wave infrared light, mid-wave infrared light, long-wave infrared light, terahertz, millimeter wave, wireless or other parts of the electromagnetic spectrum. The EM radiation may be generated by a radiation source. The radiation source may be, for example, one or more micro light emitting diodes. The radiation source may be integrated into the image sampler, may be disposed adjacent to the image sampler, or may be disposed so that radiation is transmitted through a scene and received by the image sampler. The radiation source may be a light emitting source. In one embodiment of the invention, the radiation source may be the scene itself, e.g. in case of a bioluminescent sample being examined.

In one or more embodiments of the invention, each of the masks may be a planar structure disposed between the image sampler and a scene. In one or more embodiments of the invention, the masks may include regions that are opaque and other regions that are transparent to EM radiation. The opaque and transparent regions may cause EM radiation that is incident on the mask to be partially reflected away from the image sampler and partially transmitted to the image sampler.

In one or more embodiments of the invention, the masks may include regions that have different refractive indices or thickness of transparent materials. The different regions having different refractive indices or thickness may generate amplitude and phase modulation of incident EM radiation. EM radiation that is transmitted to the image sampler may be diffracted and/or amplitude/phase modulated when compared to EM radiation that is incident on the masks.

In one or more embodiments of the invention, the mask may be disposed at a predetermined distance from the image sampler. The predetermined distance may be, for example, 500 nm. In one or more embodiments of the invention, the predetermined distance is less than 1 µm. In one or more embodiments of the invention, the predetermined distance is less than 5 µm. In one or more embodiments of the invention, the predetermined distance is less than 500 µm. In one or more embodiments of the invention, a spacer may be disposed between the mask and the image sampler. The spacer may be transparent or translucent to EM radiation to which the image sampler is responsive. The invention is not limited to the aforementioned examples.

In one or more embodiments of the invention, the image sampler processor may generate an image of the scene based on the electronic signals received from the image sampler. In one or more embodiments of the invention, the image sampler processor may be a sensor processor. The image sampler processor may be, for example, a digital signal processor (DSP), a general purpose processor, an application integrated circuit, a field-programmable gate array, an analog circuit, or any other type of electronic circuit. In one or more embodiments, the electronic signals may be received directly from the image sampler. In one or more embodiments, the electronic signals may be stored on a storage and retrieved from the storage by the image sampler processor. The image sampler and image sampler processor may be disposed at different locations without departing from the invention.

In one or more embodiments, the scene may be disposed adjacent to the mask, or in close proximity to the mask, e.g. at a distance less than 5 mm from the mask. For example, a specimen, sample, or other object of interest may be placed in close proximity to the mask. In one or more embodiments, the scene may be disposed directly adjacent to the mask. For example, a specimen, sample, or other object of interest may be placed in direct contact with the mask. In one or more embodiments of the invention, the scene may be a biometric identifier. The biometric identifier may be a finger print. In one or more embodiments of the invention, the scene may be tissue such as muscle or nerve tissue. The nerve tissue may be, for example, brain tissue. The tissue may be in vivo. The scene may be other tissues without departing from the invention.

Additional embodiments of the invention may relate to a method of operating a lens-less imaging system. The method may include displaying a number of known scenes to the lens-less imaging system and obtaining the electrical signal produced by an image sampler while exposed to each of the known scenes. The transfer function that relates EM radiation that is radiated by an unknown scene and electrical signals produced by an image sampler of the lens-less imaging system may be determined using the obtained electrical signals.

Figure 1:
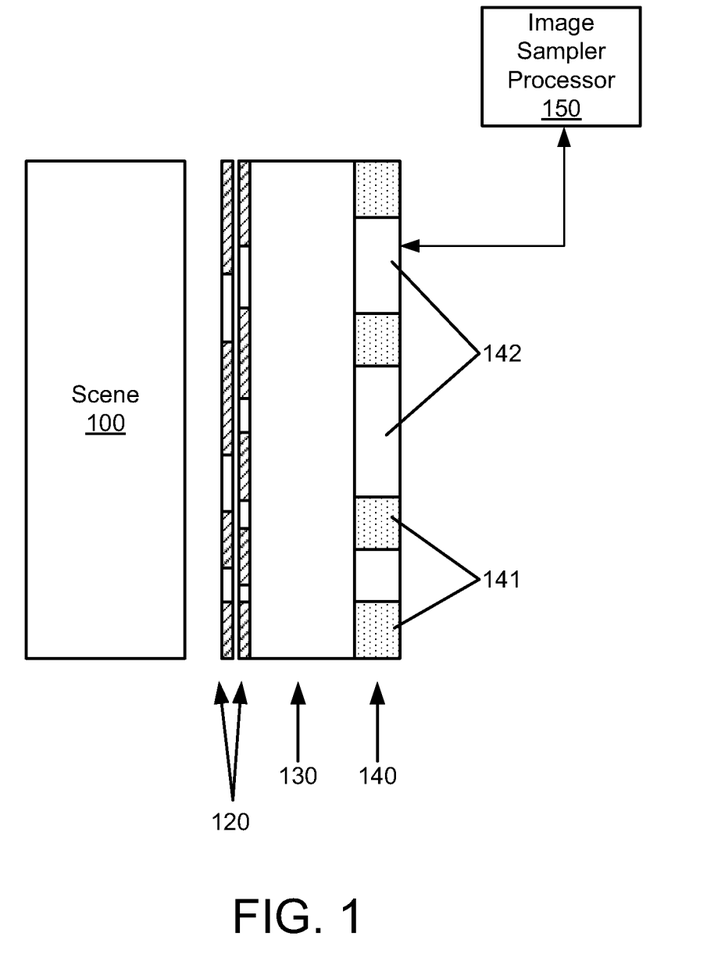
FIG. 1 shows a diagram of a lens-less imaging system in accordance with one or more embodiments of the invention.

FIG. 1 shows a lens-less imaging system in accordance with one or more embodiments of the invention. The system may be configured to generate an image of a scene (100). The system may include an image sampler (140), one or more masks (120), a spacer (130), and an image sampler processor (150). Each of the aforementioned components of the system are described below.

The image sampler (140) may be a physical device that generates electrical signals in response to incident EM radiation. In one or more embodiments of the invention, the image sampler (140) includes a number of sensing regions (142) and a number of EM radiation generation regions (141). The image sampler (140) may be operatively connected to the image sampler processor (150). The image sampler processor (150) may control the operation of the image sampler (140).

The EM radiation generation regions (141) may be, for example, light emitting diodes or organic light emitting diodes. The EM radiation generation regions (141) may be other EM radiation generating structures without departing from the invention. Portions of the EM radiation generation regions (141) may be configured to generate a first type of EM radiation, e.g., green light, while other portions maybe configured to generation a second type of EM radiation, e.g., red light. The EM radiation generation regions (141) may be divided into any number of regions that each generate different types of radiation without departing from the invention.

The sensing regions (142) may each be, for example, a charge-coupled device (CCD) or a CMOS device that generates an electrical signal when exposed to EM radiation. The sensing regions (142) may generate electrical signals that represent an amplitude, phase, and/or frequency of received EM radiation. In one or more embodiments of the invention, the sensing regions (142) may be divided into portions. Each of the portions may be tuned to have a high degree of sensitivity to a predetermined frequency of EM radiation.

Figure 4:
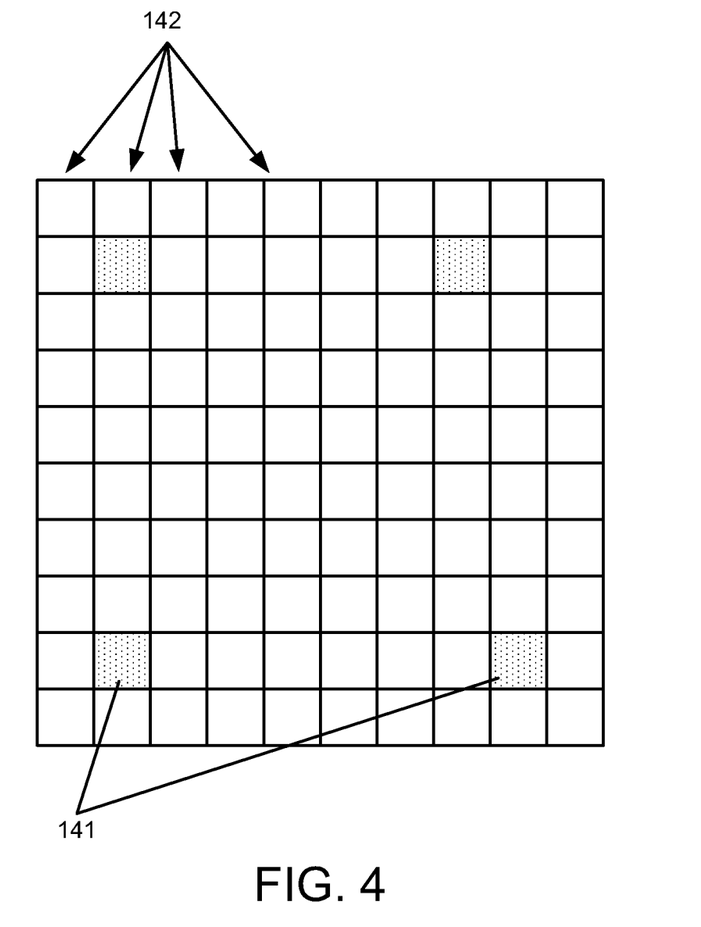
FIG. 4 shows a diagram of an exemplary image sampler in accordance with one or more embodiments of the invention.

FIG. 4 shows an example of an image sampler in accordance with one or more embodiments of the invention. The image sampler (140) includes a number of sensing regions (142) that each generate electrical signals in response to EM radiation incident on each region. For example, EM radiation may be incident on a first EM sensing region and a second EM sensing region. The first EM sensing region may produce a first electrical signal and the second EM sensing region may produce a second electrical signal. Each of the signals may be proportional to a magnitude and/or frequency of the EM radiation that is incident on each EM sensing region.

The sensing regions (142) of the image sampler (140) may be disposed over a two-dimensional (2D) area. While the sensing regions (142) are shown as square regions in a uniform 2D grid, the sensing regions (142) may have other shapes and may be distributed in a uniform or irregular pattern over the surface without departing from the invention. In one or more embodiments of the invention, the 2D area may be a flat surface. In one or more embodiments of the invention, the 2D area may be a curved surface.

The image sampler (140) also includes a number of EM radiation generation regions (141) that each generate EM radiation. The EM radiation may illuminate a scene disposed on the masks (120). The operation of the EM radiation generation regions (141) may be controlled by the image sampler processor (150) by sending instructions to the image sampler (140) via the operable connection.

In one or more embodiments of the invention, the sensing regions (142) of the image sampler (140) may generate electrical signals in response to visible light. In one or more embodiments of the invention, the sensing regions (142) of the image sampler (140) may generate electrical signals in response to infrared radiation. In one or more embodiments of the invention, the sensing regions (142) of the image sampler (140) may generate electrical signals in response to ultraviolet light, short-wave infrared light, mid-wave infrared light, long-wave infrared light, wireless, millimeter wave or terahertz radiation. The sensing regions (142) of the image sampler (140) may generate electrical signals in response to EM radiation having other spectral content without departing from the invention. Those skilled in the art will appreciate that the image sampler (140) may be sensitive to any type of radiation, including electromagnetic and particle radiation, ionizing and non-ionizing radiation, and combinations thereof. The imagine sampler may, for example, be sensitive to multiple wavelengths to produce a color image.

In one or more embodiments of the invention, at least one EM radiation generation region of the EM radiation generation regions (141) may be interposed between the sensing regions (142). In one or more embodiments of the invention, at least one EM radiation generation region of the EM radiation generation regions (141) may be disposed adjacent to at least one sensing region of the sensing regions (142). In one or more embodiments of the invention, the EM radiation generation regions (141) may be spatially dispersed to illuminate a scene. For example, each of the EM radiation generation regions (141) may be disposed in a grid pattern. In another example, each of the EM radiation generation regions (141) may be disposed in an outline pattern. The outline pattern may be, for example, the outline of a box, circle, rectangle, or any other shape. The EM radiation generation regions (141) may be disposed in other patterns to illuminate the scene without departing from the invention.

Returning to FIG. 1, the system may include one or more masks (120). The masks (120) may be a physical device that masks portions of the image sampler (140) from EM radiation that is incident on the masks (120). The masks (120) may be disposed between the scene (100) and the image sampler (140) and thereby mask portions of the image sampler (140) from EM radiation from the scene (100). A spacer (130) may be disposed between the masks (120) and the image sampler (140). In one or more embodiments of the invention, the thickness of the spacer is less than 500 nm. In one or more embodiments of the invention, the thickness of the spacer is less than 1000 nm. In one or more embodiments of the invention, the thickness of the spacer is less than 5000 nm. In one or more embodiments of the invention, the thickness of the spacer is less than 500 μm. The invention is not limited to the aforementioned distances. A glass plate may further be disposed between the mask (120) and the sample (100). The glass plate may form a cover of the lens-free imaging system and the sample may be placed over the glass plate. The glass plate may further be a slide, e.g., a slide that contains a biological sample such as tissue, blood, etc. The glass plate may further be or form a channel for flow cytometry, enabling a fluid used to transport cells or other material across the lens-free imaging system.

Figure 5:
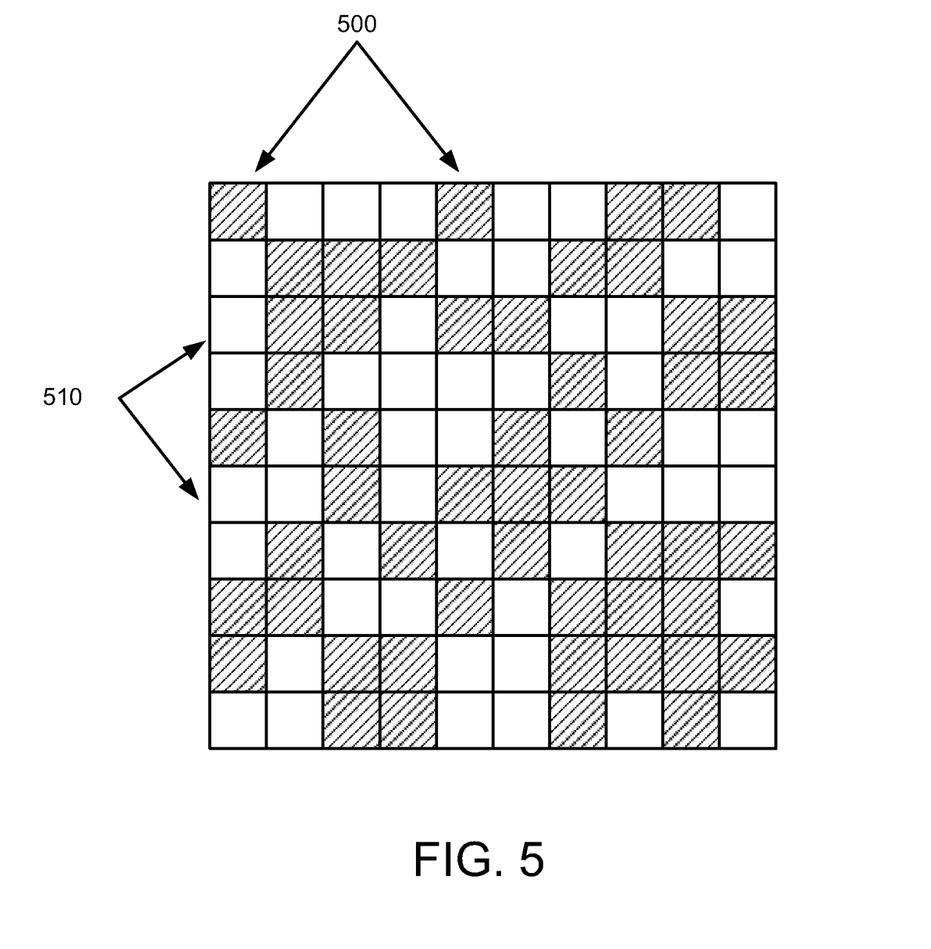
FIG. 5 shows a diagram of an exemplary mask in accordance with one or more embodiments of the invention.

FIG. 5 shows a diagram of an example of a mask of the masks (120) in accordance with one or more embodiments of the invention. In one or more embodiments of the invention, the mask is a two-dimensional pattern of refractive index changes that change the effective path length of radiation through the mask of radiation through the mask. In one or more embodiments of the invention, the mask is a two-dimensional pattern of amplitude-changing elements that change the effective transparency to radiation through the mask. In one or more embodiments of the invention, the mask is a two-dimensional pattern of phase-changing that change the effective phase of radiation through the mask. In one or more embodiments of the invention, the mask is a two-dimensional pattern of scatterers that change the direction of radiation through the mask. In one or more embodiments of the invention, the mask is a three dimensional volumetric pattern. In one or more embodiments of the invention, the mask is dynamic and changes over time.

In one or more embodiments of the invention, the mask may include first regions (500) that are opaque and second regions (510) that are transparent. The opaque first regions (500) may prevent the transmission of EM radiation through the mask and the transparent second regions (510) may allow the transmission of EM radiation through the mask.

In one or more embodiments of the invention, opaque first regions (500) may be gold, aluminum, chrome, or other metals. In one or more embodiments of the invention, the transparent second regions (510) may be glass, quartz, or may be a void space.

In one or more embodiments of the invention, the mask includes first regions (500) that have refractive indices or thicknesses that are different than the refractive indices and/or thicknesses of second regions (510) that are transparent. The first regions (500) and the second regions (510) may amplitude and/or phase module EM radiation that is transmitted through the mask.

In one or more embodiments of the invention, the first regions (500) and the second regions (510) may be distributed over a two dimensional surface. Each region may be disposed adjacent to other regions. While the first regions (500) and second regions (510) are shown in FIG. 5 in a specific two dimensional pattern, the first regions (500) and second regions (510) may be distributed in other two dimensional patterns or randomly distributed without departing from the invention.

In one or more embodiments of the invention, the first regions (500) and second regions (510) are distributed across the mask specified by the pattern M in the following equation:

$$M = \frac{1 + m_1 m_2^T}{2}, \quad (1)$$

where matrix M is of dimensions N×N. In one embodiment of the invention, $m_1$ and $m_2$ are each 1D sequences where each element is either +1 (transparent, member of the first regions (500)) or −1 (opaque, member of second regions (510)). Because opaque apertures block light, they may be assigned the value "0", in equation 1.

A separable mask pattern, composed of the cross-product of two 1D functions simplifies the calibration and image reconstruction process, as further described below, in accordance with one or more embodiments of the invention.

In one or more embodiments of the invention, 50% of the elements of the mask pattern M specify 0, e.g., an opaque region, and 50% of the elements of the mask specify 1, e.g., a transparent region.

In one or more embodiments $m_1$ and $m_2$ are random sequences where each element of the sequence specifies +1 or −1. In one or more embodiments $m_1$ and $m_2$ are maximum length sequences. In one or more embodiments $m_1$ and $m_2$ establish a modified uniform redundant array (MURA).

In one or more embodiments of the invention, there may be an equal number of first regions (500) and second regions (510). In other words, if there are 8000 first regions (500) there are 8000 second regions (510).

In one or more embodiments of the invention, each opaque region (500) and each transparent region (510) may have a square cross section. The square cross section of each region may have an edge length of the feature size of each region. In other words, a feature size of 30 nm indicates that each region is a 30 nm×30 nm square.

In one or more embodiments of the invention, the masks (120) may be disposed on a transparent support structure. The transparent support structure may be, for example, a quartz wafer.

Returning to FIG. 1, the system may include an image sampler processor (150). The image sampler processor (150) may be a physical device. The image sampler may estimate a scene based on electrical signals received from the image sampler (140) and control the operation of the image sampler (140). Specifically, the image sampler processor (150) may activate/deactivate the EM radiation generation regions (141) of the image sampler (140).

Figure 6:
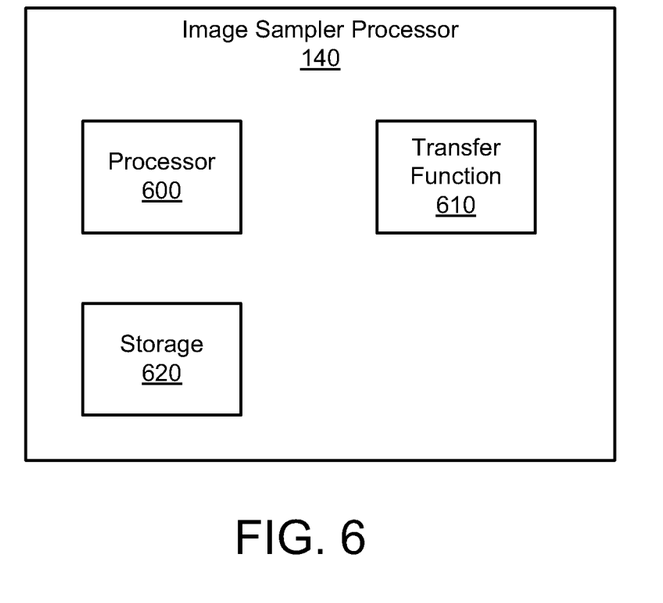
FIG. 6 shows a diagram of an image sampler processor in accordance with one or more embodiments of the invention.

FIG. 6 shows a diagram of an image sampler processor (150) in accordance with one or more embodiments of the invention. The image sampler processor (150) may be configured to and/or programmed to generate estimates e.g., images, of a scene (100) based on electrical signals received from the image sampler (140). The image sampler processor (150) may include a processor (600), transfer function (610), and storage (620). Each of the aforementioned components of the system are described below.

In one or more embodiments of the invention, the processor (600) may be a general purpose processor, embedded processor, programmable gate array, digital signal processor, or any other type of data processing device.

The storage (620) may be a non-transitory computer readable storage including instruction that, when executed by the processor (600), cause the image sampler processor (150) to perform the functionality shown in FIGS. 8 and 9, and described below. While the storage (620) is illustrated as being part of the image sampler processor (150), the storage (620) may be remote without departing from the invention.

When executing the instructions stored on the storage (620), the image sampler processor (150) may generate an estimate e.g., an image, of the scene (100) based on a relationship between EM radiation scattered by the scene (100) and the electrical signals generated by the image sampler (140). When EM radiation interacts with the scene (100), it may be scattered. A portion of the scattered EM radiation may be scattered toward the system as scene EM radiation.

When scene EM radiation is incident on the system, the masks (120) may scatter some of the scene EM radiation away from the image sampler (140) as reflected EM radiation and may scatter some of the scene EM radiation towards the image sampler (140) as transmitted radiation. The reflected EM radiation does not interact with the image sampler (140) while the transmitted EM radiation interacts with the image sampler (140), e.g., causes the image sampler (140) to generate electrical signals. The transmitted EM radiation may be modulated and diffracted by the masks (120) when compared to the scene EM radiation. Modulating and diffracting the transmitted EM radiation may multiplex the transmitted radiation onto a number of sensing regions of the image sampler.

Figure 3:
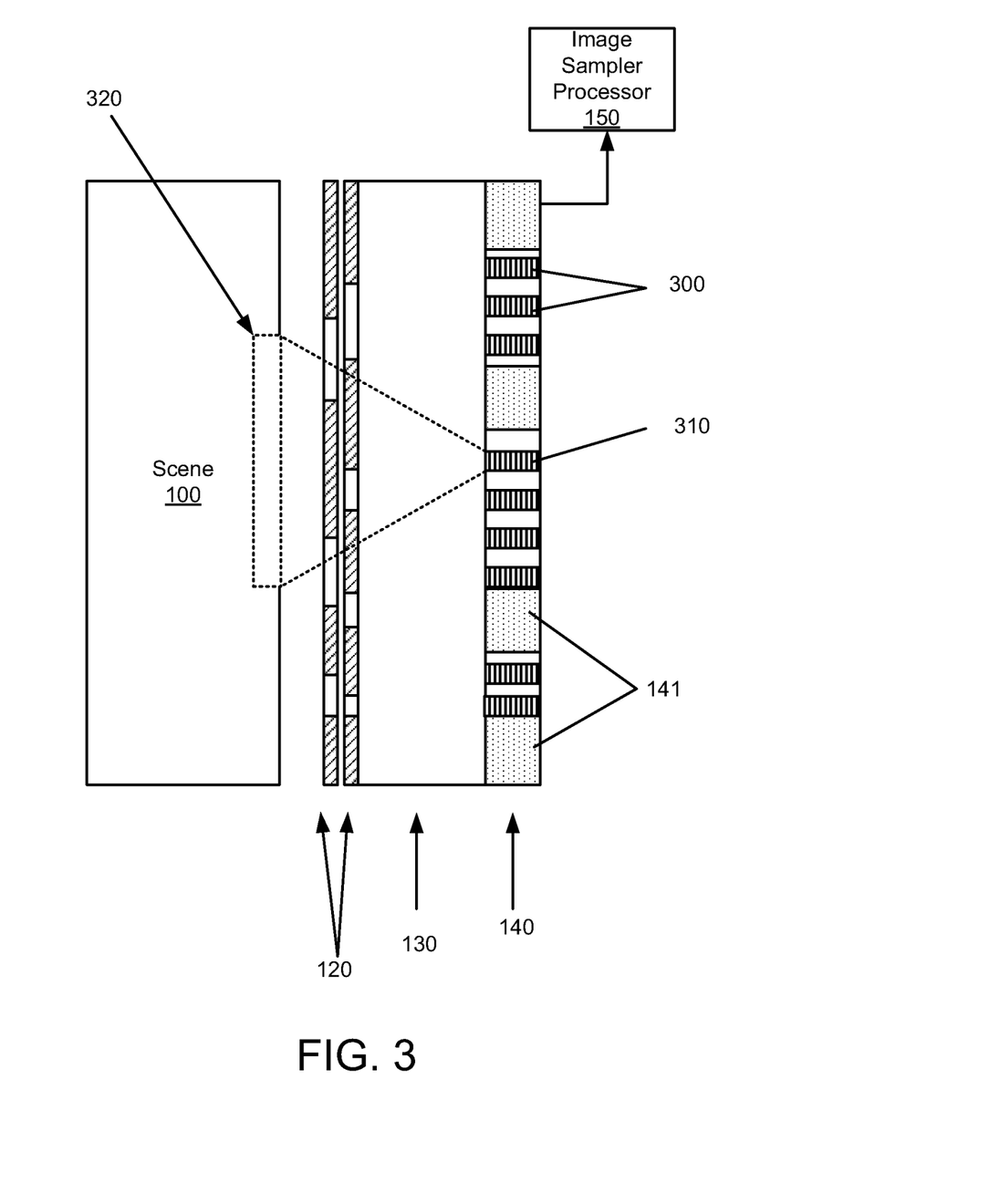
FIG. 3 shows a diagram of the system of FIG. 1 in accordance with one or more embodiments of the invention.

Additionally, when the scene is disposed directly on the masks (120), each sensing region of the scene only receives scene radiation from a portion of the scene. For example, as shown in FIG. 3, the image sampler (140) includes a number of sensing regions (300). An example sensing region (300) only receives EM radiation from a portion of the scene (320) due to the proximity of the scene. When the scene (100) is disposed close to the image sensor, a portion of the EM radiation scattered by the scene (100) is incident on the masks at an oblique angle that causes the portion of the EM radiation to scatter away from the image sampler (140) rather than be transmitted toward the image sampler (140). In contrast, when a scene is disposed away from the masks, all of the EM radiation scattered by the scene is normally incident on the mask which enables transmission of the scattered EM radiation to the image sampler (140).

To generate an image of the scene (100), it may be assumed that the scene includes a number of EM radiation sources equal to the number of features of the masks (120). In other words, if the mask is a 100×100 feature array, it may be assumed that the scene consists of 100×100 radiation sources.

Based on the above and further assuming that a separable mask pattern, composed of the cross-product of two 1D functions, as previously described, is used, the local spatially varying point spread function can be decomposed into two independent, separable terms. The first term models the effect of a hypothetical "open" mask (no apertures), and the second term models the effect due to the coding of the mask pattern. For a 2D (i.e., planar sample $X_d$, at depth d, the transfer function between the planar sample (i.e., the scene (100)) and the electrical signals generated by the image sampler (140) is:

$$Y=P_{od}X_dQ_{od}^T+P_{cd}X_dQ_{cd}^T, \quad (2)$$

in accordance with an embodiment of the invention. $P_{od}$ and $P_{cd}$ may operate only on the rows of $X_d$, and $Q_{od}$ and $Q_{cd}$ may operate only on the columns of $X_d$. The subscripts o and c refer to "open" and "coding," respectively. Importantly, the total number of parameters in $P_{od}$, $Q_{od}$, $P_{cd}$ and $Q_{cd}$ is $O(N^2)$ instead of $O(N^4)$. Thus, calibration of a moderate resolution lens-less imaging system with a 1 megapixel sensor requires the estimation of only ~4×10$^6$ rather than 10$^{12}$ elements, and image reconstruction requires roughly 10$^9$ instead of 10$^{18}$ computations.

In one embodiment of the invention, equation 2, which is specific to a planar 2D sample $X_d$ at depth d, is generalized to 3D space. For a 3D volumetric sample $X_D$, a series of planar samples $X_d$ for D different depths may be superpositioned to obtain measurements for the 3D volume. Equation 2, for the 3D generalization, thus, becomes $$Y=\Sigma_{d=1}^D(P_{od}X_dQ_{od}^T+P_{cd}X_dQ_{cd}^T). \quad (3)$$

The image of the scene may be determined by inverting equations 2 or 3, assuming the calibration matrices are known. For example, the image of the scene may be determined by recording the electrical signals of the image sampler (140) when the system is exposed to scene EM radiation. Equations 2 and 3 may be inverted using any method such as a least-squares technique or other regularized least-squares techniques. An appropriate regularization may be chosen based on the scene. For example, for extended scenes such as the USAF resolution target, a Tikhonov regularization may be used. For a given depth d and calibrated matrices $P_{od}$, $Q_{od}$, $P_{cd}$ and $Q_{cd}$, the estimated scene, $\hat{x}_d$, may be obtained by solving the Tikhonov regularized least squares problem:

$$\hat{X}_d=\arg\min_{X_d}\|P_{od}X_dQ_{od}^T+P_{cd}X_dQ_{cd}^T-Y\|_2^2+\lambda_2\|X_d\|_2^2. \quad (4)$$

Further, for sparse scenes such as a double slit, $\hat{x}_d$, may be obtained by solving the Lasso problem:

$$\hat{X}_d=\arg\min_{X_d}\|P_{od}X_dQ_{od}^T+P_{cd}X_dQ_{cd}^T-Y\|_2^2+\lambda_1\|X_d\|_1. \quad (5)$$

For the previously discussed 3D case, the Lasso problem is:

$$\hat{X}_D=\arg\min_X(\Sigma_{d=1}^D\|P_{od}X_dQ_{od}^T+P_{cd}X_dQ_{cd}^T-Y\|_2^2)+\lambda_1\|X_d\|_1. \quad (6)$$

In equations 4-6, the second term is a regularization term in which $\lambda_1$ and $\lambda_2$ control a tradeoff between fidelity and regularization.

Other methods may alternatively be used to invert equations 2 and 3, without departing from the invention. For example, if the calibration matrices are well-conditioned, the simple least-squares problem $$\hat{X}_d=\arg\min_{X_d}\|P_{od}X_dQ_{od}^T+P_{cd}X_dQ_{cd}^T-Y\|_F^2, \quad (7)$$

where $\|\;\|_F$ denotes the Frobenius norm, may be solved.

Iterative techniques may be used to solve these above optimization problems.

For example, gradient methods such as Nesterov's gradient method or a fast iterative shrinkage-thresholding algorithm (FISTA) or any other methods suitable for solving the above optimization problems may be used.

In one or more embodiments of the invention, it may be assumed that unforeseen debris or other imperfections may be incorporated into the system. The imperfections may cause aberrations or other artifacts. Embodiments of the invention may remove such aberrations by assuming the presence of error in the received EM radiation from the scene:

$$Y=\tilde{Y}+E \quad (8)$$

where $\tilde{Y}$ is the aberration free measurement and E is the aberration. Assuming that the aberration is localized, E will be a sparse matrix. Based on these assumptions, $\tilde{Y}$ may be estimated as:

$$\min_{\tilde{Y}}\|\tilde{Y}\|_*+\beta\|\tilde{E}\|_1, \text{ subject to } \tilde{Y}+E=Y. \quad (9)$$

An aberration free estimate of the scene radiance may be generated using the above equations by substituting $\tilde{Y}$ for Y.

In one or more embodiments of the invention, the calibration matrices may be determined by modeling of the modulation and diffraction of EM radiation due to the masks (120). For example, the masks (120) may be modeled computationally to determine how light from a scene (100) is distributed onto the Image sampler and thereby determine the calibration matrices. In one or more embodiments of the invention, the calibration matrices may be determined by the method shown in FIG. 8.

Figure 2:
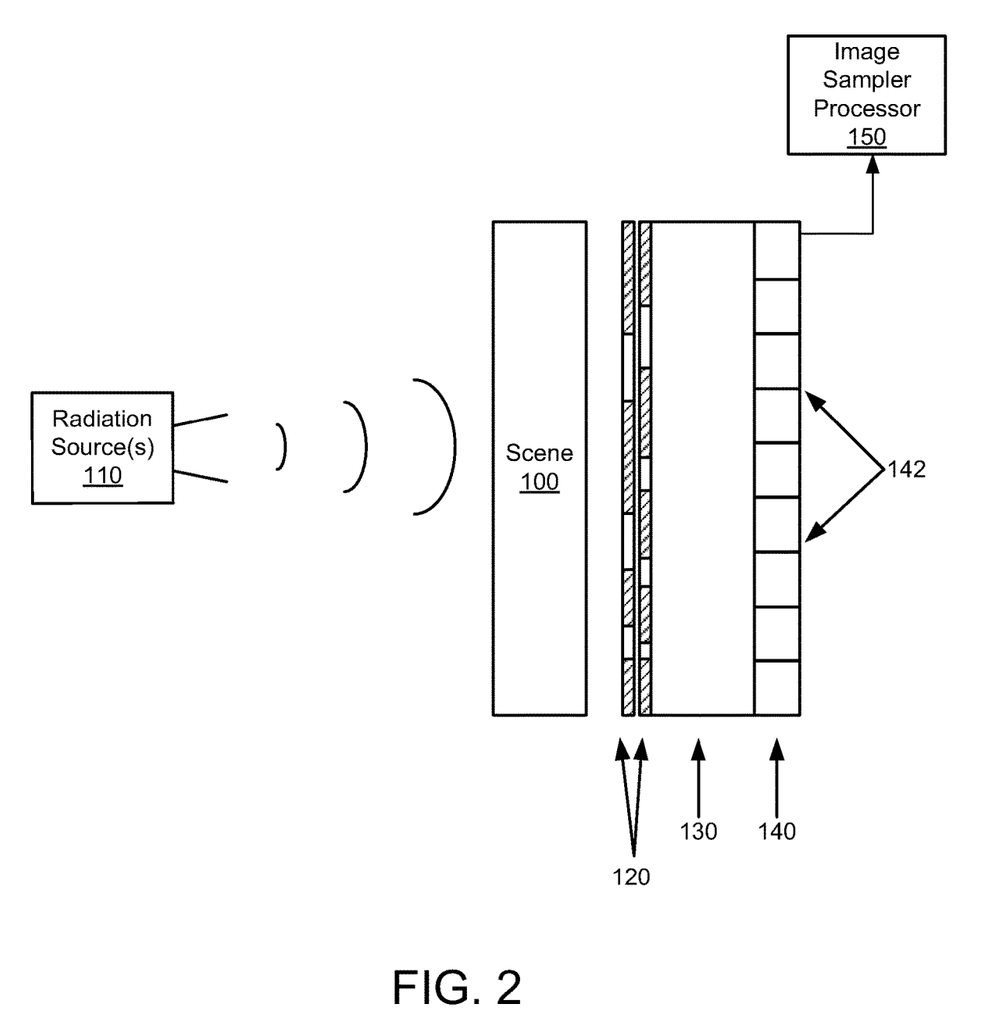
FIG. 2 shows a diagram of a second lens-less imaging system in accordance with one or more embodiments of the invention.

Numerous variations on the system shown in FIG. 1 are possible without departing from the invention. FIG. 2 shows another embodiment of a lens-free imaging system in accordance with embodiments of the invention. The system shown in FIG. 2 may be configured to image translucent and/or transparent specimens. Like-numbered elements shown in FIG. 2 perform the same function as like-numbered components in FIG. 1. The system of FIG. 2 includes radiation source(s) (110) disposed on a side of the scene (100) opposite the masks (120). The radiation source(s) (110) may be, for example, an incandescent source, a light emitting diode, or any other EM radiation producing device. In one or more embodiments of the invention, the illumination sources (110) may be ambient illumination.

Radiation generated by the radiation source(s) (110) may be transmitted through the scene (100) to the image sampler (140). Transmission through the scene (100) may modulate the radiation and thereby encode information of the scene into the radiation received by the image sampler (140). The image sampler (140) shown in FIG. 2 may include sensing regions (142) and may not include EM radiation generation regions (141, FIG. 1).

An exemplary lens-less imaging system, in accordance with one or more embodiments of the invention, may be manufactured as follows. A 100 nm thin film of chromium is deposited onto a 170 μm thick fused silica glass wafer and is subsequently photolithographically patterned. The chromium is then etched, leaving the MURA pattern with a minimum feature size of 3 μm. The wafer is diced to slightly larger than the active area of the imaging sensor. The imaging sensor may be, for example, a Sony IMX219 sensor, which provides direct access to the surface of the bare sensor. The diced amplitude mask is rotationally aligned to the pixels of the imaging sensor under a microscope to ensure that the previously discussed separability assumption is appropriate. The amplitude mask is then epoxied to the sensor using a flip chip die bonder. To filter light of a particular wavelength, an absorptive filter may be added by cutting the filter to the size of the mask and by attaching it, using, for example, an epoxy and a flipchip die bonder in the same manner. The device may further be conformally coated with a <1 μm layer of parylene for insulation.

Further, because the separability of the mathematical model is based on light propagation through a homogeneous medium an attempt is made to reduce large changes of the refractive index between the scene and the interface of the lens-less imaging system. A large change of the refractive index (e.g., due to an air-to-glass transition) may result in a mapping of lines in the scene to curves at the sensor plane, thus reducing the applicability of the separability assumption. In contrast, relatively smaller changes of the refractive index (e.g., in water-to-glass and/or biological sample-to-glass interfaces) only minimally affect the model. For calibration and image capturing, a refractive index matching immersion oil (e.g., Cargille 50350) may, thus, be applied between the surface of the mask and the target.

Figure 8:
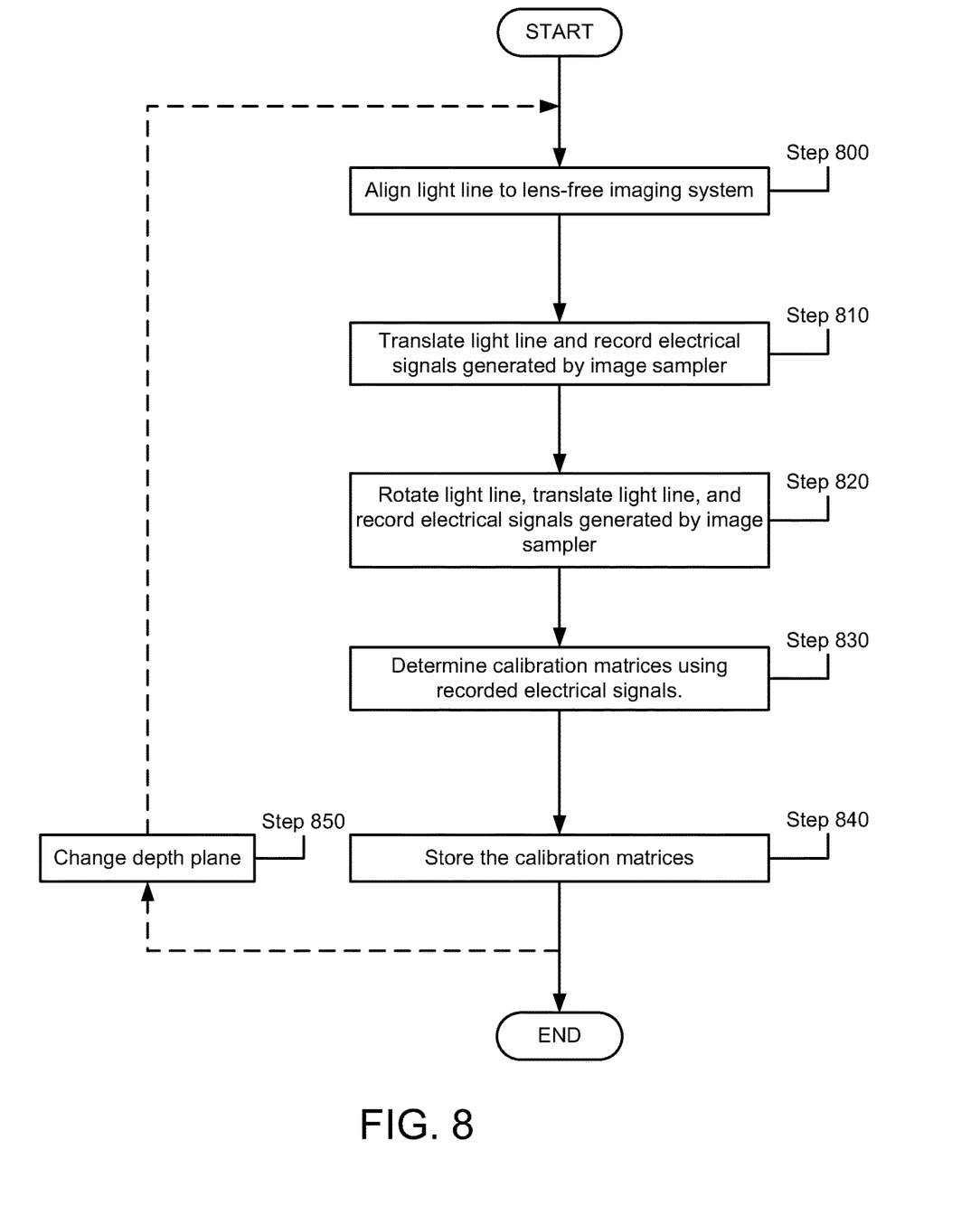
FIG. 8 shows a flowchart of a method for calibrating a lens-free imaging system in accordance with embodiments of the invention.

FIG. 8 shows a flowchart of a method in accordance with one or more embodiments of the invention. The method depicted in FIG. 8 may be used to establish a transfer function of a lens-free imaging device in accordance with one or more embodiments of the invention. One or more steps shown in FIG. 8 may be omitted, repeated, and/or performed in a different order among different embodiments.

Figure 7A:
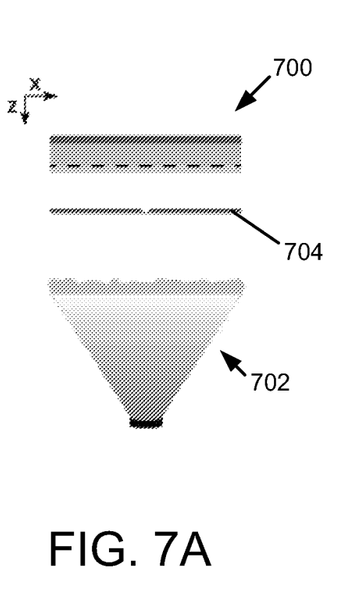
FIGS. 7A-7C shows calibration setups in accordance with embodiments of the invention.
Figure 7B:
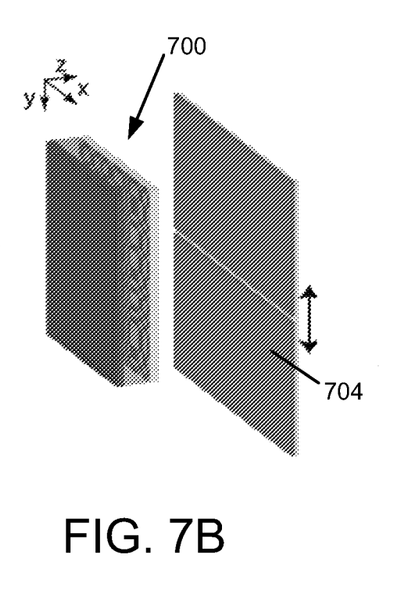
Figure 7C:
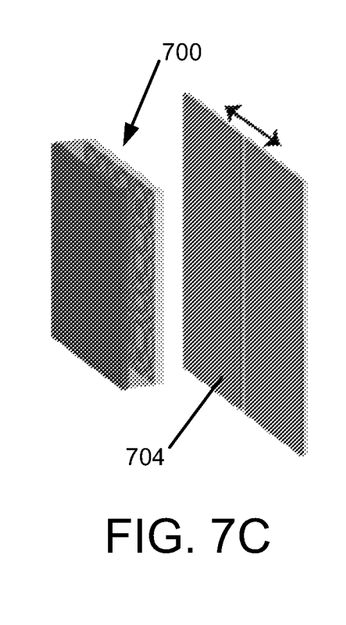

Prior to reconstructing a 3D volume from a single lens-less imaging system measurement, a calibration may need to be performed in order to identify the transfer functions (or calibration matrices) $\{P_{od}, Q_{od}, P_{cd}, Q_{cd}\}^{\{d=1, 2, \ldots, D\}}$. As previously noted, these transfer functions, in accordance with an embodiment of the invention, are separable. Accordingly, to estimate these transfer functions for a particular single lens-less imaging system, images from a set of separable calibration patterns may be captured, as illustrated in FIGS. 7A-7C. Because the calibration patterns that are displayed are separable, each calibration image depends solely on either the row operation matrices $\{P_{od}, P_{cd}\}^{\{d=1, 2, \ldots, D\}}$ or the column operation matrices $\{Q_{od}, Q_{cd}\}^{\{d=1, 2, \ldots, D\}}$ thus significantly reducing the number of images to be processed for a calibration. Using a truncated singular value decomposition (SVD), the rows and columns of $\{P_{od}, QP_{cd}, P_{cd}, Q_{cd}\}^{\{d=1, 2, \ldots, D\}}$ may be estimated as follows.

The calibration of the lens-less imaging system, in accordance with one or more embodiments of the invention, relies on the characteristic that if the scene is separable (rank-1), then the measurement obtained by the lens-less imaging system is rank-2. For example, if the scene has only the $i^{th}$ row active (or illuminated), then the scene may be written as $X_i = e_i 1^T$, where $e_i$ is a sequence of zeros with only the $i^{th}$ element to be 1 and $1^T$ is a sequence of all 1 s. Then the measurement of the lens-less imaging system may be written as:

$$Y_i = (P_o e_i)(Q_o 1)^T + (P_c e_i)(Q_c 1)^T = p_{oi} q_o^T + p_{ci} q_c^T \qquad (9)$$

Here, $p_{oi}$ and $p_{ci}$ are the it columns of $P_o$ and $P_c$, respectively, and $q_o$ and $q_c$ are the sums of columns of $Q_o$ and $Q_c$, respectively. $p_{Oi}$ and $p_{ci}$ are orthogonal and may be computed (up to a scaling factor) via the Singular Value Decomposition (SVD) of $Y_i$ truncated to the two largest singular values. Since the sensor measurements are always positive, the truncated SVD of $Y_1$ yields one vector with all positive entries and another vector with both positive and negative entries. The positive vector may be assigned to $p_{oi}$, and the other vector may be assigned to $p_{ci}$. By scanning the rows of the scene, one may compute all the entries in $P_o$ and $P_c$. Similarly, the columns of $Q_0$ and $Q_c$ may be calibrated by scanning along the columns of the scene. Scanning the rows and columns of the scene may be physically done by translating a line slit, as shown in FIGS. 7A-7C. The transfer functions $\{P_{od}, Q_{od}, P_{cd}, Q_{cd}\}$ are dependent on the distance of the scene d and may be calibrated for each depth by first translating the line slit to the required depth and then scanning the field of view. The number of calibration images needed is, thus, equal to sum of number of columns and number of rows of scene X. If the scene is of size N×N, then the number of calibration images needed is 2N. As those skilled in the art will appreciate, this is significantly less than the $N^2$ number of calibration images needed for a generalized linear model.

The calibration procedure may be independently performed for each depth plane d. Given a measurement Y and the separable calibration matrices $\{P_{od}, Q_{od}, P_{cd}, Q_{cd}\}^{\{d=1, 2, \ldots, D\}}$, a regularized least squares reconstruction algorithm may be used to recover either a 2D depth plane $X_d$ or an entire 3D volume $X_D$. The gradient steps for this optimization problem are computationally tractable due to the separability of the model.

The following flowchart illustrates the steps performed when executing the above operations. The steps are illustrated with reference to FIGS. 7A-C, which illustrate lens-less imaging system (700) being calibrated using a line slit (704), illuminated by a light source (702). The line slit, illuminated by the light source, generates a light line. In an exemplary embodiment, a 5 μm wide line slit, fabricated in a 100 nm film of chromium on a glass wafer is used. An LED array (green 5050 SMD) located ~10 cm away from the line slit is further used as a light source. To ensure that the light passing through the calibration slit is representative of a group of mutually incoherent point sources, a wide-angle diffuser (Luminit 80°) is placed between the line slit on the wafer and the light source. In FIGS. 7A-7C, the lens-less imaging system remains static, while the calibration slit, diffuser and LED array are translated with linear stages/stepper motors, separately along the x-axis and y-axis. For the calibration, the horizontal and vertical slits are translated over the field of view of the lens-less imaging system, determined by the acceptance profile of the pixels in the imaging sensor. In the exemplary system, a translation step distance of 2.5 μm was repeated at different depth planes ranging from 160 μm to 1025 μm (to perform a calibration for 3D imaging), while a translation step distance of 1 μm was used for a single depth of 150 μm (to perform a calibration for 2D imaging).

Turning to FIG. 8, in Step 800, the light line is aligned to the lens-free imaging system. The light line may be, for example, a slit in a metal film and a light source disposed on a side of the metal film opposite the lens-free imaging system, as shown in FIGS. 7A-7C. Other types of light lines may be used without departing from the invention.

In Step 810, the light line is translated along the lens free imaging system, as illustrated in FIG. 7B, and electrical signals are recorded during the translation. As the light line is translated, snap shots of the electrical signals are recorded as the light line is aligned with each row of sensing regions of the image sampler.

In Step 820, the light line is rotated to be aligned with a column of sensing regions of the image sampler that is perpendicular to a row of sensing regions of the image sampler that the light line was aligned with before the rotation. The light line is translated along the lens free imaging system and the electrical signals are recorded during the translation. As the light line is translated, snap shots of the electrical signals are recorded as the light line is aligned with each column of sensing regions of the image sampler.

Thus, during steps 810 and 820, a total of 2N snap shots of the electrical signals, generated by the image sampler, are recorded, where N is the number of sensing regions along an axis of the image sampler, assuming that each axis of the image sampler has the same number of sensing regions along each axis.

In Step 830, the calibration matrices $P_{od}$, $P_{cd}$, $Q_{od}$, and $Q_{cd}$ are determined using the recorded signals, as previously described.

In Step 840, the calibration matrices are stored. The calibration matrices may be used to directly calculate the scene estimate using electrical signals generated by the image sampler.

Execution of Steps 800-840 establishes the calibration matrices for a single depth plane, suitable for imaging samples in the depth plane. If 3D volumes are to be imaged, Steps 800-840 may be repeated for other depth planes. Accordingly, in Step 850, the depth plane may be changed, e.g., by modifying the distance between the line slit (704) and the lens-less imaging system (700). Steps 800-850 may be repeated for any number of depth planes, and the obtained calibration matrices $\{P_{od}, Q_{od}, P_{cd}, Q_{cd}\}^{\{d=1, 2, \ldots, D\}}$ may subsequently be used for the imaging described in FIG. 9. The calibration matrices may remain valid, as long as the geometry of the lens-free imaging device remains unchanged.

Figure 9:
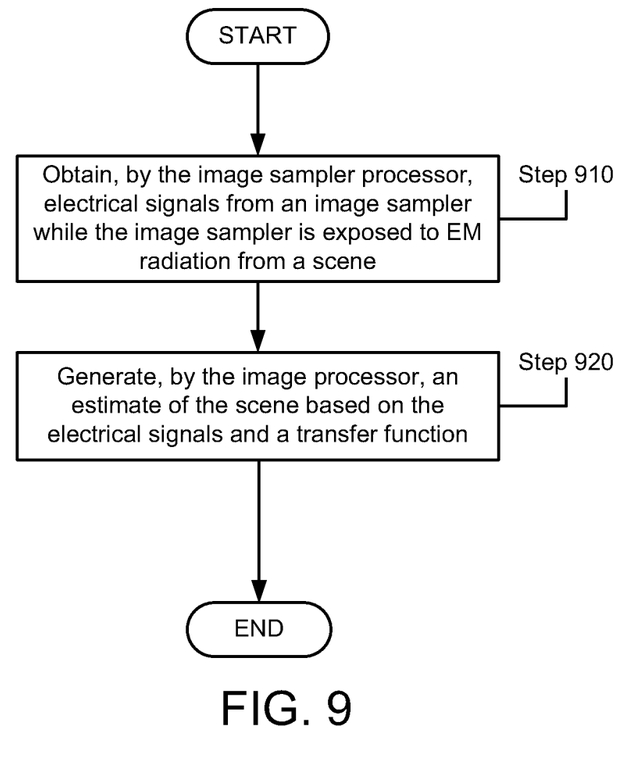
FIG. 9 shows a flowchart of a method for generating an image using a lens-free imaging system in accordance with embodiments of the invention.

FIG. 9 shows a flowchart of a method in accordance with one or more embodiments of the invention. The method depicted in FIG. 9 may be used to generate an image of a scene using a lens-free imaging device in accordance with one or more embodiments of the invention. One or more steps shown in FIG. 9 may be omitted, repeated, and/or performed in a different order among different embodiments.

In Step 900, electrical signals from an image sampler are obtained by an image sampler processor while the image sampler is exposed to EM radiation from a scene that is disposed near the masks of the image sampler. For example, the image sampler may be exposed to EM radiation for 10 milliseconds and the scene may be a finger pressed against the masks of the image sampler.

In Step 910, the image sampler processor generates an estimate of the scene based on the obtained electrical signals and a transfer function. The transfer function may be stored in the image sampler processor. The transfer function may include the calibration matrices determined using the method of FIG. 9. The transfer function may be determined prior to performing the method of FIG. 9 and may be, for example, one of the previously discussed equations 4-7, which enable reconstruction of 2D planar images or 3D volume images.

While the above description of generating an image of a scene has been for single images or stacks of images that form a 3D volume, embodiments of the invention may include generating a number of images using the above method at different points in time to generate a video. In one or more embodiments of the invention, an image of a scene at a first point in time may be used to improve the speed of reconstruction of a second image scene at a second point in time. For example, there may be little difference between images of a scene at different points in time that are temporally separated by small amounts, e.g., fractions of a second. An image of a scene at a first time that is temporally separated from an image as a scene at a second time may substantially reduce the computation power and time required to estimate a scene when compared to generating an image of a scene without a previously generated image of the scene.

One or more embodiments of the invention may provide one or more of the following advantages: (i) a system in accordance with embodiments of the invention may be used to obtain high-resolution 2D and 3D images, e.g., at micron-resolution, from a single captured frame; (ii) a system in accordance with embodiments of the invention may be significantly more compact than lens-based systems; (iii) a system in accordance with embodiments of the invention may have a significantly wider field of view than comparable lens-based systems; (iv) a system in accordance with embodiments of the invention may have a very high light collection ability; (v) a system in accordance with embodiments of the invention allows the rapid computation of an image; and/or (vi) a system in accordance with embodiments of the invention may be less expensive and/or simpler to produce when compared to lens-based imaging systems. Systems in accordance with one or more embodiments of the invention are therefore particularly suited for a variety of applications including in-vitro and in-vivo microscopy. A system may be used, for example, for 3D fluorescence imaging of large volumes spanning, e.g., multiple cubic millimeters of tissue, and/or as implantable imaging devices that minimize tissue damage while providing a wide field of view, using potentially multiple adjacently located lens-less imaging devices. Other microscopy applications include various bright-field, dark-field, reflected-light, phase contrast, bioluminescence and calcium signaling microscopy techniques. Systems in accordance with one or more embodiments of the invention may further be ideally suited for biometrics applications. Using larger imaging sensors or arrays of smaller imaging sensors, the lens-less imaging devices may be employed to capture biometrics including, but not limited to, fingerprints, vein patters, faces, iris patterns, etc.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A lens-free imaging system, comprising:
   an image sampler;
   a radiation source;
   a mask disposed between the image sampler and a scene,
      wherein the mask comprises a two-dimensional pattern of regions that alter the radiation received, through the mask, by the image sampler and from the scene, and
      wherein the two-dimensional pattern is composed of a cross-product of two one-dimensional functions, thereby making the two-dimensional pattern separable; and
   an image sampler processor that:
      obtains signals from the image sampler that is exposed, through the mask, to radiation scattered by the scene, wherein the scene is illuminated by the radiation source; and
      estimates an image of the scene based on the signals from the image sampler, processed using a transfer function that relates the signals and the scene.

2. The lens-free imaging system of claim 1, wherein the regions comprise at least one selected from a group of radiation path length changing regions, radiation amplitude changing regions, radiation phase changing regions, and regions with radiation scattering characteristics.

3. The lens-free imaging system of claim 1, wherein the transfer function comprises a first term for a hypothetical "open" mask and a second term for a hypothetical "coding" mask, based on the separable two-dimensional pattern.

4. The lens-free imaging system of claim 1, wherein the estimate of the image of the scene is performed for a single depth, thereby producing a planar two-dimensional image estimate.

5. The lens-free imaging system of claim 1, wherein the estimate of the image of the scene is performed for multiple depths, thereby producing a three-dimensional image estimate.

6. The lens-free imaging system of claim 1, wherein the scene is one selected from a group consisting of an in-vitro and an in-vivo sample.

7. The lens-free imaging system of claim 6, wherein one selected from a group consisting of fluorescence, bioluminescence, calcium signaling, bright-field, dark-field and phase-contrast microscopy is performed on the scene.

8. The lens-free imaging system of claim 6, wherein the scene is a biometric.

9. The lens-free imaging system of claim 1, wherein the scene is disposed adjacent to the mask, at a distance less than 5 mm from the mask.

10. The lens-free imaging system of claim 1, wherein the image sampler is configured to capture at least one selected from a group consisting of visible, infrared, ultraviolet, microwave, and ionizing radiation.

11. The lens-free imaging system of claim 1, wherein the image sampler is configured to capture a sequence of images at different points in time to generate a video.

12. The lens-free imaging system of claim 1 further comprising a glass plate disposed between the mask and the scene,
   wherein a sample that forms the scene is placed over the glass plate.

13. The lens-free imaging system of claim 12, wherein the glass plate is one selected from a group consisting of a slide comprising a biological sample and a flow channel for flow cytometry.

14. The lens-free imaging system of claim 1 further comprising a second image sampler,
   wherein the second image sampler is disposed adjacent to the first image sampler in order to capture a scene that extends across the first and the second image sampler.

15. A method for generating an image of a scene using a lens-free imaging system, the method comprising:
   obtaining signals from an image sampler that is exposed, through a mask, to radiation scattered by the scene; and
   estimating the image of the scene, based on the signals from the image sampler, processed using a transfer function that relates the signals and the scene,
   wherein the mask comprises a pattern that enables the separation of the mask into a hypothetical open mask and a hypothetical coding mask, and
   wherein the transfer function comprises additively superimposed terms representing the hypothetical open mask and the hypothetical coding mask.

16. The method of claim 15 further comprising obtaining the transfer function, using a calibration, prior to estimating the image.

17. The method of claim 16, wherein obtaining the transfer function comprises:
   obtaining a series of calibration signals from the image sampler that is exposed, through the mask, to radiation scattered by a series of separable calibration patterns; and
   identifying the transfer function using the series of calibration signals and the series of separable calibration patterns,
   wherein the identified transfer function establishes a relationship between the series of separable calibration patterns and the series of calibration signals, thereby enabling estimation of the scene, using the signals.

* * * * *